United States Patent [19]
Baugh

[11] Patent Number: 5,314,826
[45] Date of Patent: May 24, 1994

[54] PLATELET ACTIVATION AND FUNCTION EVALUATION TECHNIQUE

[75] Inventor: Robert F. Baugh, Parker, Colo.

[73] Assignee: Medtronic Hemotec, Inc., Englewood, Colo.

[21] Appl. No.: 749,211

[22] Filed: Aug. 23, 1991

[51] Int. Cl.$^5$ ............................................. G01N 33/86
[52] U.S. Cl. ...................................... 436/69; 436/55; 422/73
[58] Field of Search ................ 436/69, 10, 55; 422/73

[56] References Cited

U.S. PATENT DOCUMENTS

| | | | |
|---|---|---|---|
| 3,077,106 | 2/1963 | Fink | 73/53 |
| 3,302,452 | 2/1967 | Leslie | 73/64.1 |
| 3,307,392 | 3/1967 | Owen et al. | 73/64.1 |
| 3,450,501 | 6/1969 | Oberhardt | 23/230 |
| 3,492,096 | 1/1970 | Hattersley | 46/69 |
| 3,560,162 | 2/1971 | Mittleman | 23/230 |
| 3,560,163 | 2/1971 | Mittleman | 23/230 |
| 3,587,295 | 6/1971 | Simons | 73/64.1 |
| 3,635,678 | 1/1972 | Seitz et al. | 23/230 R |
| 3,650,698 | 3/1972 | Adler | 23/253 R |
| 3,658,480 | 4/1972 | Kane et al. | 23/230 B |
| 3,692,487 | 9/1972 | Sanz | 23/253 R |
| 3,695,842 | 10/1972 | Mintz | 324/65 R |
| 3,699,437 | 10/1972 | Ur | 324/65 R |
| 3,704,099 | 11/1972 | Sanz | 23/230 B |
| 3,719,075 | 3/1973 | Mandrona | 73/54 |
| 3,741,002 | 6/1973 | Simons | 73/64.1 |
| 3,814,585 | 6/1974 | Bailly | 23/230 B |
| 3,836,333 | 9/1974 | Mintz | 23/259 |
| 3,854,324 | 12/1974 | Altshuler et al. | 73/64.1 |
| 3,911,728 | 10/1975 | Fixot | 73/54.04 |
| 3,918,908 | 11/1975 | Moyer et al. | 23/230 B |
| 3,963,349 | 6/1976 | Albright et al. | 73/64.1 |
| 4,000,972 | 1/1977 | Braun et al. | 23/230 B |
| 4,026,671 | 5/1977 | Simons et al. | 23/259 |
| 4,040,788 | 8/1977 | Simons et al. | 23/230 R |
| 4,058,367 | 11/1977 | Gilford et al. | 23/253 R |
| 4,074,971 | 2/1978 | Braun et al. | 23/230 B |
| 4,081,242 | 3/1978 | Girolami | 23/230 R |
| 4,285,906 | 8/1981 | Meltzer et al. | 422/64 |
| 4,390,499 | 6/1983 | Curtis et al. | 422/72 |
| 4,443,408 | 4/1984 | Mintz | 422/73 |
| 4,533,519 | 8/1985 | Baugh et al. | 422/73 |
| 4,534,939 | 8/1985 | Smith et al. | 422/61 |
| 4,551,308 | 11/1985 | Mintz | 422/58 |
| 4,599,219 | 7/1986 | Cooper et al. | 422/61 |
| 4,612,801 | 9/1986 | Girolami | 73/64.1 |
| 4,663,127 | 5/1987 | Jackson et al. | 422/58 |
| 4,671,939 | 6/1987 | Mintz | 422/58 |
| 4,752,449 | 6/1988 | Jackson et al. | 422/73 |
| 4,780,418 | 10/1988 | Kratzer | 436/69 |
| 4,797,369 | 1/1989 | Mintz | 436/69 |
| 4,871,677 | 10/1989 | Baugh et al. | 436/69 |
| 4,876,069 | 10/1989 | Jochimsen | 436/69 |
| 5,091,304 | 2/1992 | LaDuca et al. | 436/69 |

*Primary Examiner*—James C. Housel
*Assistant Examiner*—Lien Tran
*Attorney, Agent, or Firm*—John R. Ley; Carol W. Burton

[57] ABSTRACT

The intensity of initial agitation of blood and an activating reagent affects the contribution of platelets to clotting in an activated clotting time (ACT) test. An improved ACT test accommodates the effects of platelet activation by incorporating a platelet activation phase. In the platelet activation phase an activating reagent is mixed with a sample of blood to be tested at a controlled point in time followed by gently agitating the mixture in such a manner and for a period of time sufficient to establish a predetermined and predictable contribution to the ACT from platelet activation. The platelet activation phase is followed by a clotting test phase of the ACT test. A platelet functionality test provides information regarding the functionality of platelets in a sample of blood. The platelet functionality test uses two simultaneous ACT tests, one with a platelet activation phase which normally achieves a relatively high rate of contribution from platelet activation to clotting, the other with a platelet activation phase which normally achieves a relatively lower rate of contribution from platelet activation to clotting. The difference between the ACTs of the two ACT tests is indicative of the platelet functionality of the sample of blood.

44 Claims, 7 Drawing Sheets

Fig_1

Fig_2

Fig_3

Fig_6

Fig_5

Fig_4

Fig_7

Fig_8A

Fig_8B

PLATELET ACTIVATION AND FUNCTION EVALUATION TECHNIQUE

This invention relates to measuring and detecting a coagulation and coagulation related activities in fluids, particularly human blood. More particularly, the present invention relates to an improved activated clotting time test for whole blood which accounts for platelet activation. Further, this invention relates to a clinical test for determining platelet functionality in human blood.

BACKGROUND OF THE INVENTION

Blood coagulation is a complex chemical and physical reaction which occurs when the blood comes into contact with an activating agent, such as an activating surface or an activating reagent. In accordance with one simplified conceptual view, the whole blood coagulation process can be generally viewed as three activities: agglutination of platelets, blood clotting and fibrous tissue formation. In vivo, platelets flow through the blood vessels in an inactivated state because the blood vessel lining, the endothelium, does not activate platelets. When a blood vessel is damaged, however, the endothelium loses its inert character and activates the platelets at the damage site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced which causes polymerization of fibrinogen into fibrin strands, which form the major portion of the clot mass. During clotting, additional platelets are activated and trapped in the forming clot, contributing to clot formation. As clotting proceeds, fibrous tissue is formed which serves as the permanent clot. Thus platelet activation plays a very important function in blood coagulation.

A number of different medical apparatus and testing methods exist for measuring and determining coagulation and coagulation related activities of blood. These apparatus and methods provide valuable medical information to an attending physician. For example, the information assists a physician in prescribing medication, predicting post-operative bleeding and prescribing various therapies. One of the more successful techniques of evaluating blood clotting and coagulation is a plunger technique illustrated by U.S. Pat. Nos. 4,599,219 to Cooper et al. and 4,752,449 to Jackson et al., and U.S. patent application No. 07/644,007 to Smith, filed Jan. 18, 1991, now U.S. Pat. No. 5,174,961, all of which are assigned to the assignee of the present invention, and all of which are incorporated herein by reference.

Automated apparatus employing the plunger technique for measuring and detecting coagulation and coagulation related activities generally comprise a plunger sensor cartridge or cartridges and a microprocessor controlled apparatus into which the cartridge is inserted. The apparatus acts upon the cartridge and the blood sample placed therein to induce and detect the coagulation related event. The cartridge includes a plurality of test cells, each of which is defined by a tube-like member having an upper reaction chamber where a plunger assembly is located and where the analytical test is carried out, and a lower reagent chamber which contains a reagent or reagents. For an activated clotting time (ACT) test, for example, the reagents include an activation reagent to activate coagulation of the blood. A plug member seals the bottom of a lower reagent chamber. When the test commences the contents of the lower reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends by the force of gravity, resisted by a property of the fluid in the reaction chamber, such as its viscosity. When the property of the sample changes in a predetermined manner as a result of the onset or occurrence of a coagulation related activity, the descent rate of the plunger assembly therethrough is changed. Upon a sufficient change in the descent rate, the coagulation related activity is detected and indicated by the apparatus.

SUMMARY OF THE INVENTION

Certain discoveries have recently been made which contribute to a better understanding of the role of platelets in an activated clotting time (ACT) test. Such discoveries suggest that the activation of the platelets has a significant and previously unappreciated effect on ACT test results. It has long been suspected that platelet activation contributes to total blood coagulation times, but there has been no technique available for confirming and quantifying the impact of platelet activation on ACT. It has been discovered that the initial contact and interaction of the blood sample with the activating reagent has an impact on the platelet activation, which may make the ACT test results variable and operator dependent. Without understanding and controlling the effect of platelet activation on the ACT there is a probability of inconsistent and inaccurate clinical test results. The degree and extent of the impact may depend on operator technique, but the impact and the extent of the impact has been unappreciated and unquantified. No previously known ACT test has intentionally taken into account the effect of platelet activation on the test results.

In developing and testing the improved high sensitivity coagulation detection apparatus employing the plunger technique, described in patent application Ser. No. 07/644,007, (referred to hereinafter as the resecond generation ACT apparatus") identical blood samples were tested on both the second generation ACT apparatus and the assignee's earlier apparatus, illustrated by that described by U.S. Pat. No. 4,752,449 (referred to hereinafter as the "first generation ACT apparatus"). When results obtained by the second generation ACT apparatus were compared with the results obtained from the first generation ACT apparatus, it was discovered that with identical blood samples and identical test cartridges, the second generation ACT apparatus produced consistently longer coagulation times than the first generation ACT apparatus. It was also noted that a still earlier and different version of the assignee's apparatus (referred to hereinafter as the "HMS apparatus") produced coagulation times similar to those of the second generation ACT apparatus. The principal difference noted between the first and second generation of ACT apparatus, that also differentiated the first generation ACT apparatus from the HMS apparatus, was that both the second generation ACT apparatus and the HMS apparatus reciprocate the plunger at a relatively high rate, while the first generation ACT apparatus reciprocates the plunger at a relatively slower rate, during initial mixing of the sample with the activation reagent. The faster reciprocation rate of the second generation ACT apparatus is desireable during testing because the faster rate results in increased sensitivity for detection of clot formation during the test.

While the reasons for the discoveries described herein may not be completely understood at this time, it is believed that upon initial contact of the blood with the activating reagent, the platelets are very susceptible to the amount and type of agitation they encounter. In accordance with this belief, platelets are visualized as coming into contact with activating particles and being activated at the surface of the particle. Gentle agitation resulting from a slower plunger drop rate may tend to bring the platelets into better contact with the activating particles and allow the platelets to adhere to the particles, achieving full activation. However, more violent agitation may strip the platelets from the surface of the activating reagent particles before the platelets are fully activated, thus prolonging or adding the previously unappreciated variability of some measure of uncontrolled platelet activation to the amount of time required to achieve clotting in an ACT test. As a result of this discovery concerning the role of platelets in an ACT, the present invention encompasses a clinical ACT test capable of recognizing functional platelet activation in a controlled and predictable Manner.

One significant aspect of the present invention is a method of conducting an ACT test to intentionally accommodate the rate at which platelet activation contributes to an ACT. According to this aspect of the invention, platelet activation is controllably achieved in a specific platelet activation phase of the test. In addition, the activating reagent is separated from the sample of blood to be tested until the beginning of the test. Upon beginning the test, the activating reagent is added to the sample of blood and, immediately following reagent addition, the platelet activation phase commences. The platelet activation phase comprises a predetermined time period of relatively low intensity agitation, thus activating the platelets in a controlled fashion. The length of the predetermined time period controls the degree of platelet activation. Maximum activation is preferably achieved in a plunger technique ACT test by a thirty to forty second predetermined time period of relatively low intensity agitation, as described below. The agitation in the platelet activation phase preferably maximizes platelet activation or achieves a predetermined degree of platelet activation which contributes to clotting, consistent with reliable, accurate and reproducible ACT test results. Following the platelet activation phase, the ACT test continues through a clotting test phase. The clotting test phase follows the usual procedure of the particular ACT test being performed. With the controlled platelet activation phase, the ACT test becomes less operator dependent and the ACT test results become more reliable and consistent.

Another significant aspect of the present invention is a new test to evaluate platelet functionality or establish an index of platelet functionality. According to this aspect of the invention two ACT tests, each with a controlled platelet activation phase, are performed on two samples of the same blood. The type of agitation of the platelet activation phase in the first test is selected to normally achieve a relatively higher rate of contribution from platelet activation to the ACT when performed on a normal blood sample. A normal blood sample is defined as a sample of blood containing a concentration of functional platelets typical of a human whole blood sample which does not exhibit any pathology or the effects of medication. The type of agitation in the platelet activation phase in the second test is selected to normally achieve a relatively lower rate of contribution from platelet activation to the ACT when performed on a normal blood sample. If functional platelets are present, the ACT of the first test will be shorter than the ACT of the second test. If the functional platelets are not present, the ACTS of the two tests will be approximately equal. Any difference in the two ACTs comprises a basis for computing an index of platelet functionality. This index provides information regarding the in vivo functionality of platelets and is useful information in providing appropriate medical care.

A more complete appreciation of the present invention and its scope can be obtained from understanding the accompanying drawings, which are briefly summarized below, the following detailed description of a presently preferred embodiment of the invention, and the appended claims.

DETAILED DESCRIPTION OF PREFERRED EMBODIMENT

It has been discovered that the results of activated clotting time (ACT) tests performed on blood are dependent on the degree and duration of agitation of the blood sample and the activating reagent during the initial stages of the ACT test. The degree and duration of the activation achieves a degree of activation of functional platelets and a related contribution to the ACT from a predetermined degree of platelet activation, all of which is unrelated to a kinetic acceleration of clotting due only to agitation. However, the nature of the mechanical agitation creates a specific predetermined effect on the degree and rate of platelet activation as a predetermined contribution to the ACT. The term "blood" as used herein may include whole blood and the separable components thereof, such as plasma and various concentrates, but blood must contain platelets. Unless specifically stated otherwise, or the context makes it apparent, the platelets are assumed to show some amount of normal predilection for activation.

Figure 1:
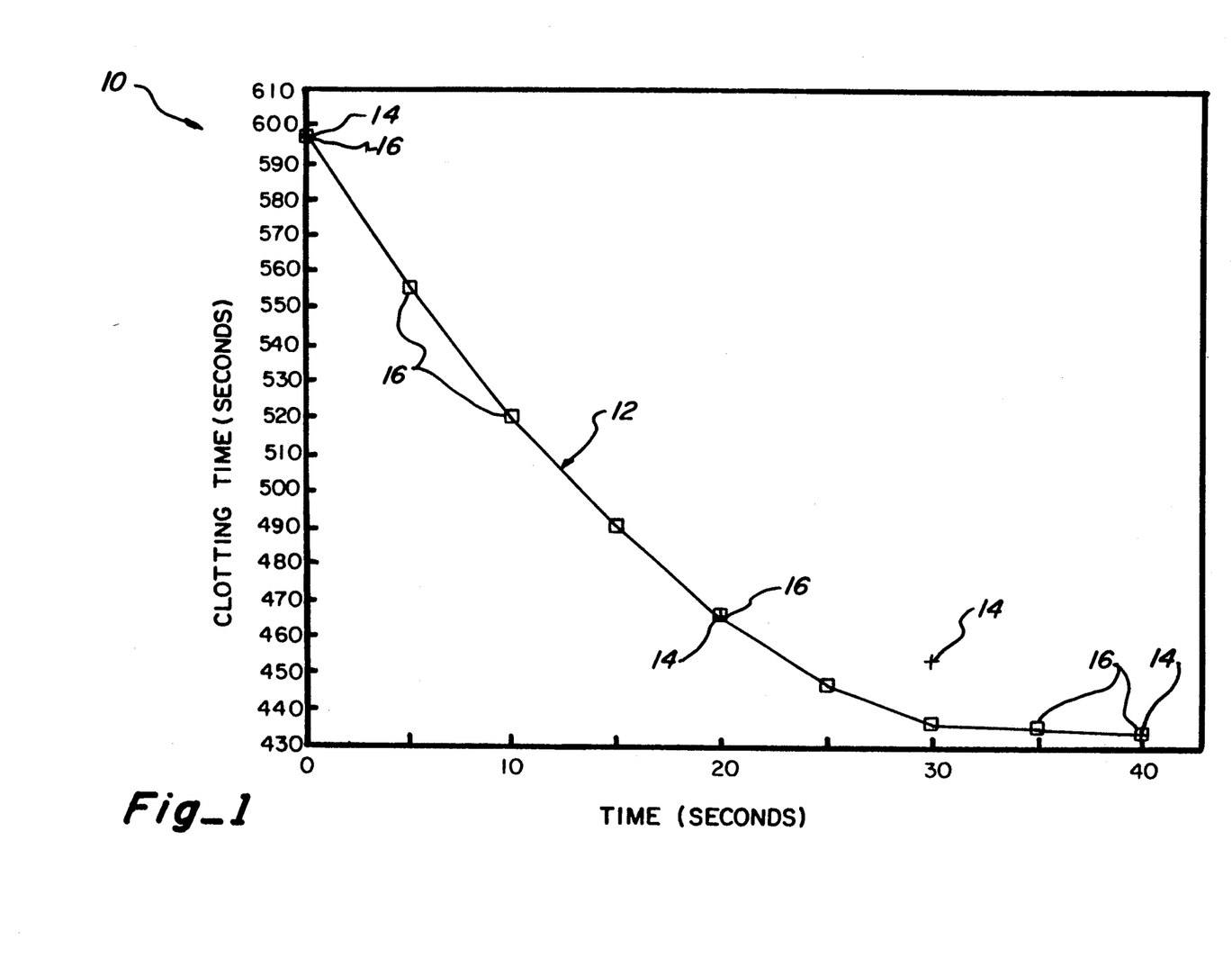
FIG. 1 is a graph which illustrates the differences in activated clotting time of a single sample of blood for varying rates of contribution from platelet activation, measured using a plunger sensor technique, the discovery of which has been recognized in accordance with the present invention.

A graph 10 shown in FIG. 1 illustrates the dependency of ACT test results on the character of initial agitation of the blood sample and the activating reagent. The graph 10 was derived from data obtained from a series of ACT tests on the blood drawn from a single individual, diluted thirty percent with lactated Ringer's solution and heparinized to four units/ml. The vertical axis of the graph 10 represents the ACT in seconds. The horizontal axis represents the length of an initial phase or period of controlled agitation in seconds, during which some contribution to the rate of platelet activation may occur. The trace 12 (located by rectangular data points 16) is a polynomial regression of the actual data obtained (located by cross data points 14). The one of the ACT tests represented by the data point on the vertical axis incorporated no initial phase or period of agitation and each of the other ACT tests incorporated an initial phase or period of controlled, relatively gentle agitation, followed by more vigorous agitation typical of the ACT phase or period of the test being performed. The nature of the agitation during the initial and subsequent phases is described below. The trace 12 illustrates the results of the ACT test for varying time durations of the initial phase of controlled agitation.

As can be seen from the graph 10, in the ACT test with no initial period of controlled agitation the ACT is longer than the ACT for each test which incorporates an initial period of controlled agitation. It can further be seen from the graph 10 that the ACT for each test with longer periods of initial controlled agitation is reduced. After an initial agitation phase of about thirty to forty seconds, with the assignee's plunger sensor apparatus, further initial agitation achieves little additional reduction or different contribution to the ACT. Thus, it appears that an initial agitation phase of approximately thirty to forty seconds with the assignee's plunger sensor apparatus achieves approximately the maximum contribution to the rate of platelet activation for an ACT.

Achieving the maximum rate of platelet activation to the ACT has the effect minimizing the potential for variable results in the ACT. However, it is not necessary to achieve a maximum rate of platelet activation in order to practice the present invention. The present invention does require, however, a controlled predetermined activation phase in which a predetermined degree of accountable platelet activation is obtained so as to be specifically taken into account in determining the ACT.

Figure 2:
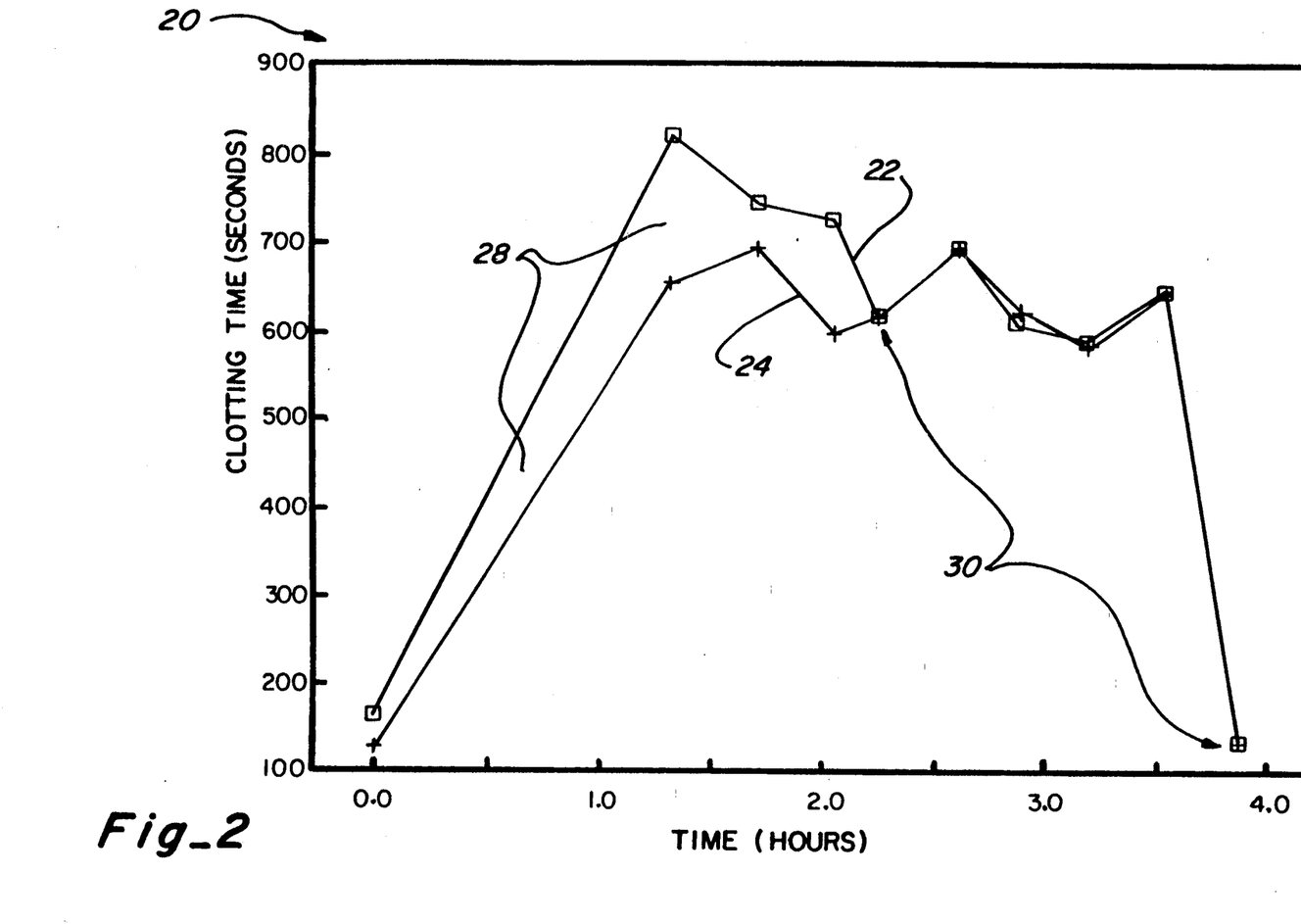
FIG. 2 is a graph which illustrates the differences in activated clotting time of two blood samples of the same blood with a relatively high rate of contribution from platelet activation and with a relatively low rate of contribution from platelet activation, measured using a plunger sensor technique, which has been recognized in accordance with the present invention.

The effect of different amounts of controlled platelet activation on an activated clotting time (ACT) test performed on typical blood samples is illustrated by a graph 20 shown in FIG. 2. The graph 20 is derived from data obtained from tests performed on blood samples obtained during coronary bypass surgery. A vertical axis of the graph represents the ACT or clotting time in seconds, and a horizontal axis of the graph represents time in hours from the beginning of the coronary bypass surgery. A top trace 22 (located by rectangular reference points) illustrates the results of a series of ACT tests performed under predetermined conditions which normally result in a predetermined low rate of contribution of platelet activation to the ACT. A bottom trace 24 (located by cross reference points) illustrates the results of a simultaneous series of ACT tests on another portion of the same sample of blood performed under predetermined conditions which normally result in a predetermined high rate of contribution from platelet activation to the ACT. The relatively high rate of contribution to platelet activation represented by the bottom trace 24 is achieved by an initial period of relatively low agitation of the sample. The relatively low rate of contribution to platelet activation represented by the top trace 22 is achieved by relatively high initial agitation of the sample. Agitation of the sample and the ACT test are preferably performed using the plunger cartridge and apparatus of the assignee as described herein.

As can be seen from the graph 20, the ACTs (trace 24) for the samples with a relatively high rate of contribution from platelet activation are generally shorter than the ACTs (trace 22) for samples with a relatively low rate of contribution from platelet activation. The difference in ACTs of the two samples is represented by an area 28 between the traces 22 and 24. That this difference area 28 is due to different rates of contribution from platelet activation was confirmed by laboratory tests wherein the blood samples tested were treated to substantially deactivate or remove the platelets from the sample using known techniques such as by chemical preactivation of platelets. When identical samples of blood with platelets removed or deactivated were tested, and when plasma was tested, it was found that the tests providing a relatively high initial agitation produced substantially the same results as simultaneous tests providing a relatively low initial agitation. Thus it has been demonstrated that the dependency of the ACT on the initial agitation of the sample is due to the activation of the platelets achieved by agitation and is not merely due to kinetic acceleration of normal blood clotting from agitation itself.

Referring to FIG. 2, the difference 28 between the two traces 22, 24 also comprises an index of platelet functionality. A greater difference 28 between the ACTs of the simultaneous tests represented by the traces 22 and 24 represents a greater degree of platelet functionality. A portion 30 of the traces 22 and 24 where the results of the simultaneous ACT tests are substantially identical is indicative of a loss of platelet functionality. This phenomenon is typical during coronary bypass surgery, due to the activation of platelets resulting from exposure of the blood to the extracorporeal bypass mechanism.

The testing that resulted in the present invention, and the applications of the present invention, are preferably achieved by the use of the Assignee's plunger technique apparatus. The initial agitation is defined by plunger. A cycle rate of approximately 0.8 seconds per cycle, a drop height of approximately 2.24 mm, and a drop rate of the plunger assembly of approximately 7.2 mm per second, are the preferred details of movement for the gentle agitation to achieve a maximum contribution to platelet activations.

The presently preferred embodiment of an apparatus 32 and a plunger sensor cartridge 34 which are used together in order to perform an ACT test with a platelet activation phase is illustrated in FIGS. 3, 4, 5 and 6. The apparatus 32 and an appropriate cartridge 34 can also be used to perform a platelet functionality index test. It is anticipated that coagulation-related testing techniques other than the plunger techniques may also be used to perform an ACT test with a platelet activation phase and the platelet functionality index test, in accordance with this invention. It is anticipated that similar results and effects as those obtained from using the assignee's plunger sensor technique will also be obtainable by practicing the present invention using other well known mechanical devices for agitating the blood sample in a controllable manner to achieve a controlled contribution from platelet activation. However, it is uncertain that the other mechanical systems will achieve equal contributions of platelet activation with equal agitation times or rates.

Figure 3:
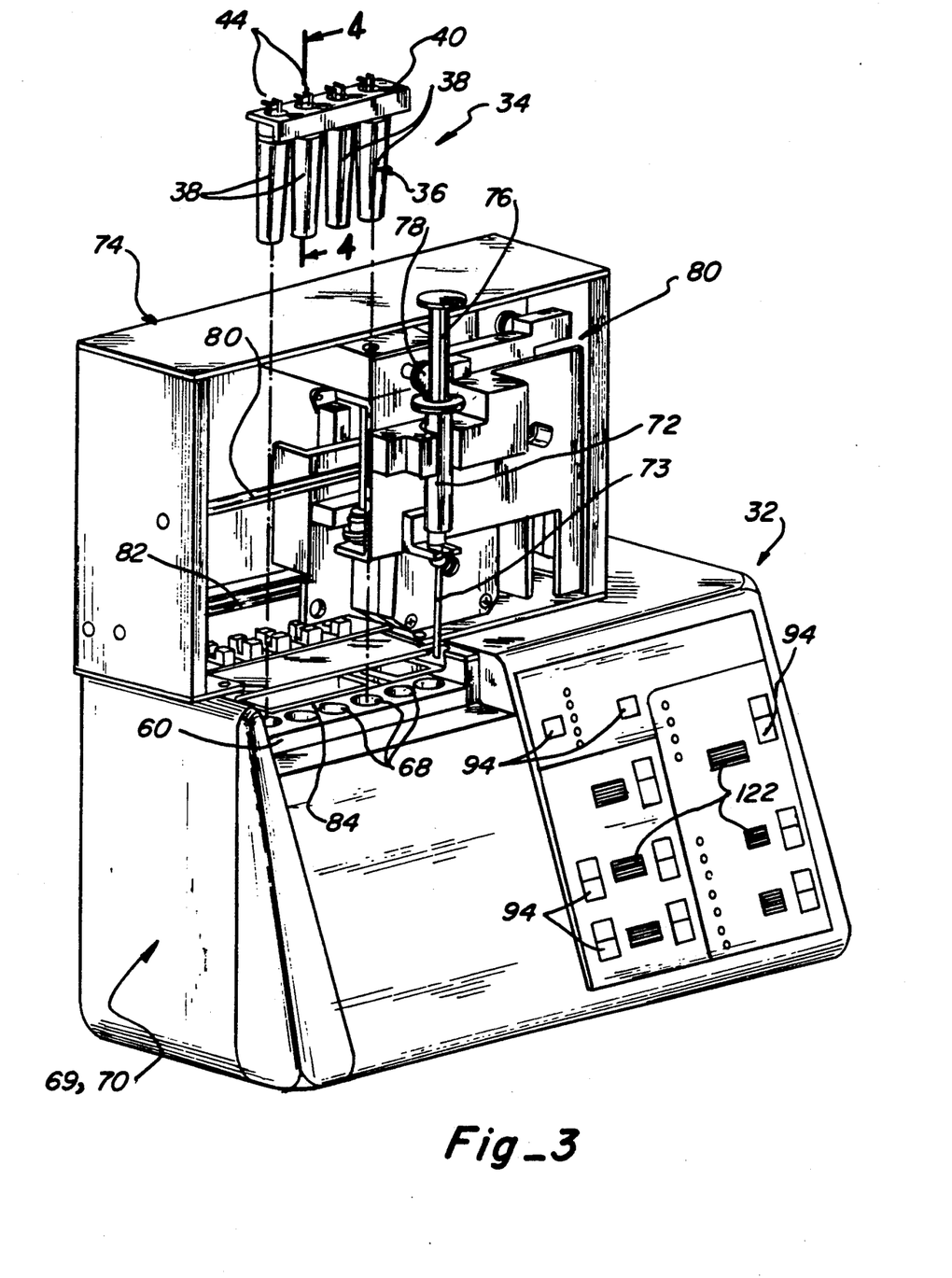
FIG. 3 is a perspective view of a high sensitivity coagulation detection apparatus and a plunger sensor cartridge used in conjunction with the apparatus, with which the present invention may be preferably practiced.
Figure 4:
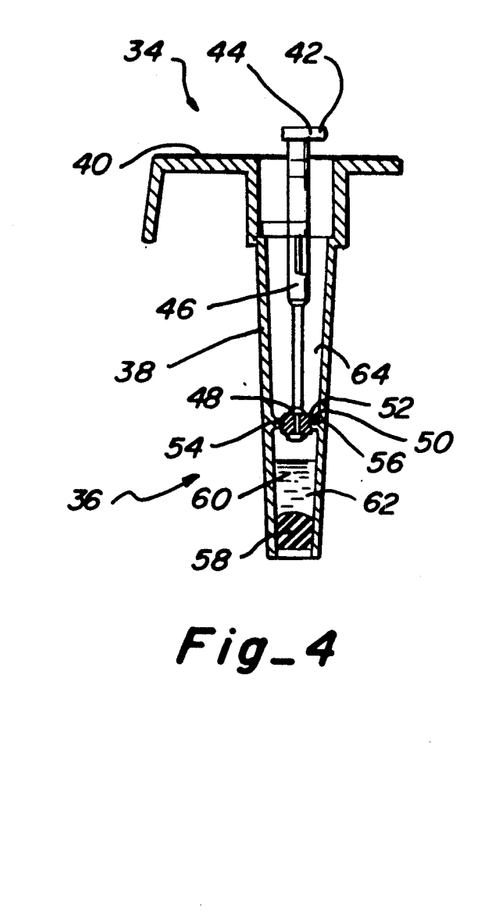
FIG. 4 is a vertical sectional view of one test cell of the cartridge shown in FIG. 3, taken substantially in the plane of line 4—4 of FIG. 3.

In general, the cartridge 34, as shown in FIGS. 3 and 4, includes a plurality of test cells 36, each of which is formed generally as a downward extending truncated tube-like member 38. Each of the tube-like members 38 is connected to an upper shelf portion 40. A plunger assembly 42 extends downward from an upper open end of each test cell 36 into the tube-like member 38. Each plunger assembly 42 includes at least one and preferably a pair of flags 44 at the upper end located at a position above the shelf portion 40. The plunger assembly 42 also includes a shaft 46 which extends from the flags 44 downward to a lower end upon which a disk member 48 is attached. The disk member 48 is formed of resilient material and includes a center generally cylindrical main body portion 50 and an annular flange 52 located above and extending outward from the main body portion 50. The annular flange includes slots or openings (not shown) formed therein at outer circumferential locations.

As shown in FIG. 4, prior to using the plunger sensor cartridge 34 in the apparatus 32, the disk member 48 is positioned with its main body portion 50 located in and sealed against an opening 54 formed by a partition 56 extending inwardly from the tube-like member 38. The partition 56 is located between the upper and lower open ends of the tube-like member 38. A resilient flexible plug 58 is positioned in the interior of the tube-like member at its lower open end. The plug 58 seals against the inner side walls of the tube-like member 38 and confines a quantity of reagent 60, comprising the activation reagent in the case of an ACT test, in a reagent chamber 62 between the partition 56 and the plug 58. The reagent 60 may be a liquid or a solid powder. A reaction chamber 64 is generally defined by that portion of the open tube-like member 38 above the partition 56.

Figure 5:
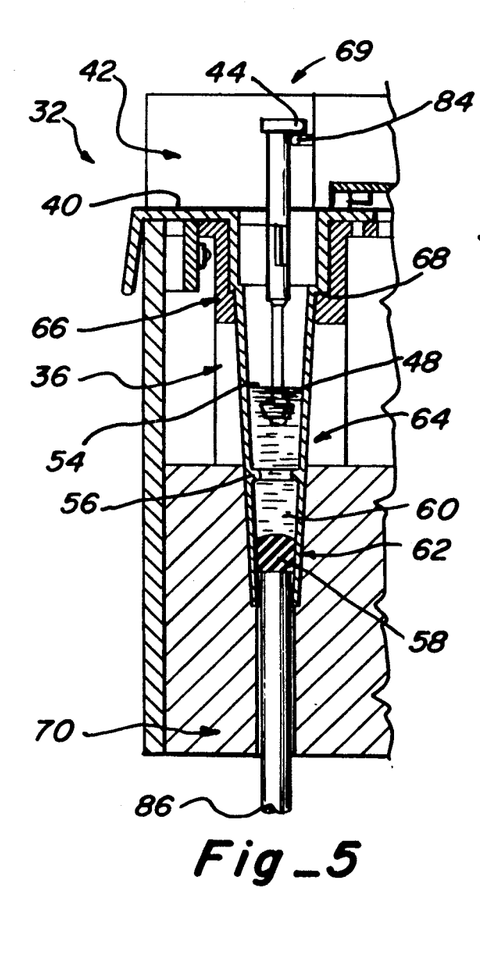
FIGS. 5 and 6 are sectional views similar to those shown in FIG. 4, illustrating the elements of the apparatus and the test cell of the cartridge at the commencement of, and during the course of, an ACT test performed in accordance with the present invention.
Figure 6:
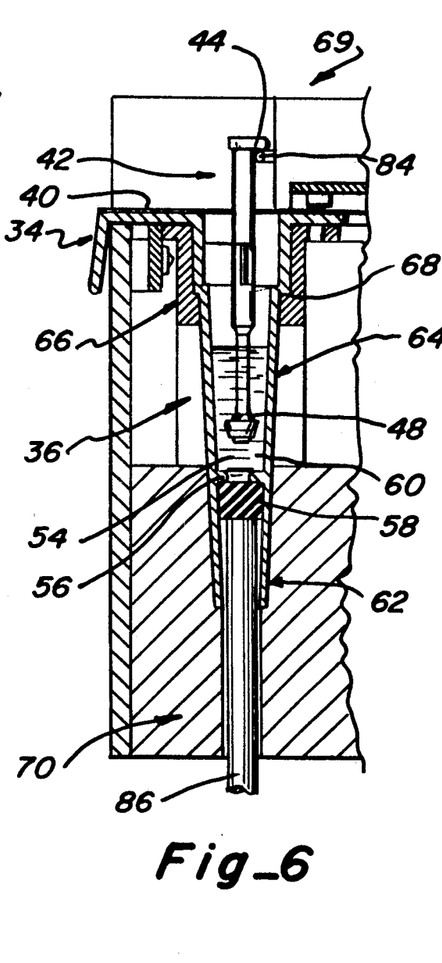

The plunger sensor cartridge 34 is inserted into a receiving block 66 in the apparatus 32 to conduct the ACT test, as is shown in FIGS. 4, 5 and 6. Each of the test cells 36 extends into a receptacle 68 of the receiving block 66. Each receptacle 68 was a configuration adapted to receive a test cell 36, while the shelf portion 40 of the cartridge 34 sits on top of the block 66.

The apparatus 32 is generally formed of subassemblies. A plunger lifting subassembly 69 of the apparatus 32 controls the lifting movement of the plunger assembly 42, and a reagent drive subassembly 70 of the apparatus 32 moves the plug 58 to force the reagent 60 into the reaction chamber 64. A dispensing subassembly 74 of the apparatus 32 automatically supplies a sample of blood to each test cell 36 of the cartridge 34. An optical sensing system (not shown) senses the physical descent of the plunger assembly through the sample and reagent in the reaction chamber 64 in order to detect coagulation condition.

The sample of blood is supplied to the reaction chamber from a syringe 72 having a blunt needle 73 attached thereto. The syringe 72 is manually attached to the dispensing subassembly 74 of the apparatus 32. The body of the syringe 72 contains blood, preferably fresh drawn from the patient, upon which the ACT test is to be performed. Of course, prior to attachment of the syringe 72 to the dispensing subassembly 74, all air or other voids in the fluid within the syringe 72 and the blunt needle 73 is removed in the conventional manner. A plunger 76 located within the body of the syringe 72 is engaged with a drive wheel 78. Rotation of the drive wheel 78 forces the syringe plunger 76 downward and expels a predetermined amount of blood from the lower end of the blunt needle 73. The extent to which the syringe plunger 76 is moved downward determines the quantity of fluid expelled from the needle.

The dispensing subassembly 74 includes a movement frame 80 which is moved laterally in the horizontal direction along guide rods 82. The degree of lateral movement is controlled by the microprocessor (not shown) of the apparatus 32 in accordance with programmed information, thereby locating the blunt needle 73 directly above the open upward ends of each test cell 36 of the cartridge 34. After attaining the proper lateral location, the movement frame 80 moves the syringe 72 vertically downward to insert the lower end of the blunt needle 73 into each of the test cells 36. The desired amount of fluid sample is automatically dispensed into the test cell 36. Thereafter, the blunt needle 73 is withdrawn from the test cell 36 by the movement frame 80, and the next lateral position over a test cell is assumed. The sequence again repeats itself, thereby injecting into each test cell 36 of the plunger sensor cartridge 34 that predetermined amount of blood sample needed for conducting the ACT test.

A portion of the plunger lifting subassembly 69 is shown in FIGS. 3, 5 and 6, and includes at least one and preferably a plurality of lift wires 84. The lift wires 84 are positioned in a lowermost location, and in that position a horizontal segment of the lift wires fits underneath the flags 44 of the plunger assembly 42. Upward movement of the lift wires 84 lifts each of the plunger assemblies 42 upward, thereby removing the disk member 48 from its sealed location in the opening 54 of the partition 56 as is shown in FIG. 5. A fluid communication passageway through the opening 54 between the reagent chamber 62 and the reaction chamber 64 is thereby established. The reagent drive subassembly 70 includes a plurality of plug driver shafts 86. Thereafter, or simultaneously with the upward movement of the plunger assembly 42, the plug driver shafts 86 of the reagent drive subassembly 70 move upward, forcing each plug 58 upward collapsing the reagent chamber 62 and forcing its contents 60 into the reaction chamber 64. This condition is illustrated in FIG. 6.

At the commencement of an ACT test, a sample of blood upon which the test is to be performed is introduced into the reaction chamber 64. The lift wires 84 of the subassembly 69 lift the plunger assembly 42 to withdraw the disk member 48 from its seated engagement with the opening 54 in the partition 56, as shown in FIG. 5. The plug 58 is pushed upward against the partition 56 by the plug driver shafts of the subassembly 70. The reagent 60 from the reagent chamber 62 is forced through the opening 54 into the reaction chamber 64, as shown in FIG. 6. The reagent 60 is mixed with the fluid sample in the reaction chamber, by reciprocating the plunger assembly 42. Many of the details of the functionality of the apparatus 32 used to perform these tests have been generalized, with the understanding that the applicant's prior patents and application disclose these details to a greater extent.

Figure 7:
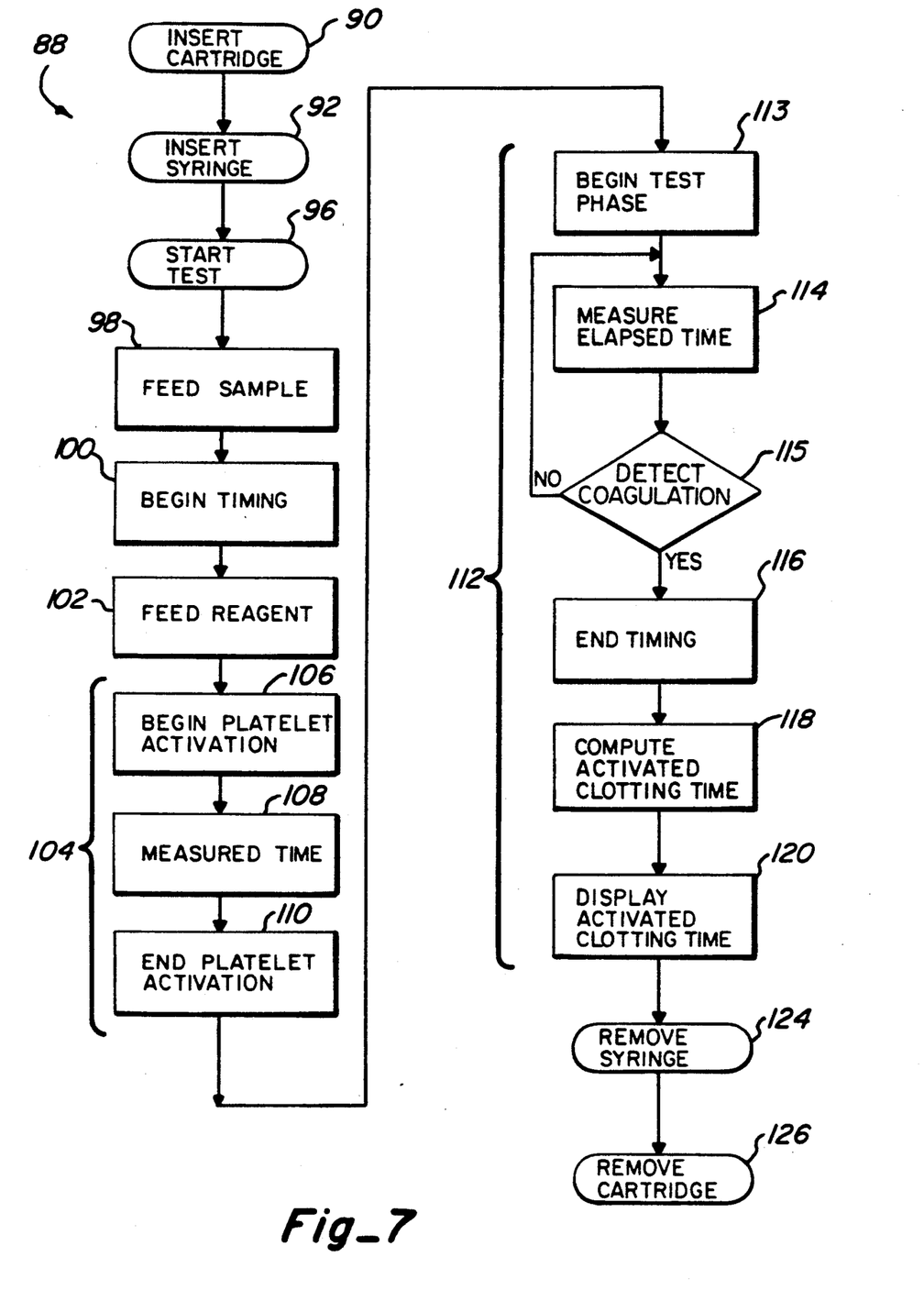
FIG. 7 is a flow chart of a preferred form of an activated clotting time test with a controlled platelet activation phase in accordance with the present invention.

A preferred form of an ACT test 88 with a controlled platelet activation phase performed with the plunger technique apparatus 32 and cartridge 34 is shown in FIG. 7 and described in conjunction with FIGS. 3 and 4. The steps in the ACT test 88 shown in FIG. 7 will be referred to below by reference numbers enclosed in parenthesis. The plunger sensor cartridge 34 is first inserted (90) into the apparatus 32 into the receiving block 66 of the apparatus 96. A syringe 72 filled with the blood sample to be tested is then inserted (92) into the sample dispensing subassembly 74 of the apparatus 32. The operator enters any required information utilizing a plurality of control switches 94 (FIG. 3) on the exterior housing of the apparatus 32 and begins the test (96) by depressing one of the control switches 94. A precise predetermined amount of blood s injected ample is then fed or injected (98) into the reaction chamber 64 of a cell 36 of the test cartridge 34, preferably by the sample dispensing subassembly 74. After the predetermined amount of blood sample is fed into the reaction chamber 64 the microprocessor of the apparatus begins timing the ACT test (100). Simultaneously, the plunger lifting subassembly 69 lifts the plunger assembly 42 and the reagent drive subassembly 70 forces the plug 58 of the test cell upward, thereby feeding reagent (102) into the reaction chamber 64 and creating a test mixture of the blood sample and the reagent. In this manner the blood sample in the reaction chamber 64 is kept separate from an activating reagent 60 in the reaction chamber 62 until the commencement of the test, thereby starting a predetermined and established rate of contribution of platelet activation to ACT at the same controlled point in time in each of the reaction chambers of the cartridge and with respect to the ACT test conducted on each blood sample. The reagent in the cartridge comprises a platelet activation reagent such as kaolin. Immediately following the feeding of the reagent (102) into the reaction chamber 64, a platelet activation phase (104) commences (106).

The platelet activation phase (104) occurs over a predetermined measured time period (108), for example thirty to forty seconds. Platelet activation begins (106) by starting a relatively low intensity of agitation of the blood sample by reciprocating the plunger assembly 42 (FIG. 4) at a predetermined relatively slow rate, preferably at a cycle rate of approximately 0.8 seconds per cycle, a reciprocation distance of approximately 2.24 mm, and a drop rate of approximately 7.2 mm per second. The repeated lowering of the plunger assembly causes agitation to mix the fluid sample and the reagent in the test mixture during the platelet activation phase. The rate of lowering the plunger assembly during the platelet activation phase (104), and thus the intensity of agitation, is predetermined to bring platelet, into substantially complete contact with the activating reagent while at the same time limiting the hydrodynamic forces within the sample to avoid stripping the platelets from the activating reagent before the platelets are activated, thus preferably promoting a full contribution of platelet activation to the ACT. The agitation preferably continues at the same rate throughout until the platelet activation phase (104) ends (100).

The intensity or rate of the agitation during the platelet activation phase is selected SO that the ACTs achieved are reliable#accurate and repeatable, and to enhance the clinical utility of the results. It is not necessary that all platelets in the sample be completely activated or that the platelets be activated to maximize the contribution of platelet activation to the ACT during the platelet activation phase. It is sufficient that the platelet activation phase activate the platelets in such a manner that the "rate of contribution of platelet activation to the ACT be predetermined, reproducible and predictable when performed on a sample of normal blood. In this manner the ability to make clinically useful comparisons among ACT test results is enhanced. In circumstances where less than the maximum rate of contribution to the ACT is achieved from a predetermined degree of platelet activation, it may be possible to compensate the measured ACT in relation to the degree of predictable contribution actually achieved in the platelet activation phase. Such compensation may result in an estimate of the ACT for a maximum or other predetermined degree of platelet activation. In other applications where the predetermined maximum rate of contribution of platelet activation to the ACT is achieved, no compensation to the measured ACT is believed necessary.

Following the end of the platelet activation phase (104) the ACT test continues according to its usual clotting test phase (112). It is preferred that the time of the platelet activation phase is included in the ACT. In the case of the preferred plunger technique ACT, the plunger lifting subassembly 69 reciprocates the plunger assembly 42 at an increased rate to achieve greater sensitivity. This clotting test phase rate is approximately one cycle per second or two percent of the total run time, with a drop height of approximately 6.35 mm and a plunger descent rate of approximately 46.8 mm per second, to achieve high sensitivity ACT testing. At the beginning (113) of the clotting test phase (112), another time measurement is commenced (114).

As a property of the test mixture changes during the clotting test phase (112), the descent of the plunger assembly 42 relative to the lowering movement of the lift wire 84 changes. Since the tube-like member 38 of each test cell 36 is formed of clear material such as plastic, optical sensors which are located within the interior of each receptacle 68 of the receiving block 66, are used for the purpose of monitoring the descent of the plunger assembly 42 relative to the descent of the lift wire 84, once a change of a predetermined magnitude is detected (115), clotting and the ACT of the sample is determined to have occurred. Upon detection of the predetermined change, timing stops (116) and the ACT is computed (118) and displayed (120) on a display 122 (FIG. 3) present on the outside housing of the apparatus 32. In the preferred form of the ACT test 88, the ACT is computed as the total time from the beginning of timing (100) until timing ends (116) upon detection of coagulation (114). The operator then removes the syringe 72 (124) and cartridge 34 (126) at the conclusion of the ACT test with platelet activation phase (88).

By separating the sample of blood from contact with the activating reagent until commencement of the ACT test, and by controlling the intensity of agitation of the sample during the platelet activation phase, the platelets are activated in a predetermined controlled manner so as to establish a predictable rate of their contribution to the ACT. By controlling the rate of contribution of platelet activation to ACT, more reliable, accurate and repeatable ACT test results occur. The effects of operator variability are eliminated and the clinical usefulness of the test is increased. Further, by controlling the rate of contribution of platelet activation to the ACT through the predetermined platelet activation phase, it is possible to combine the slow agitation required for a high rate of contribution of platelet activation to clotting with the more rapid agitation required to achieve high sensitivity in an ACT test.

Figure 8A:
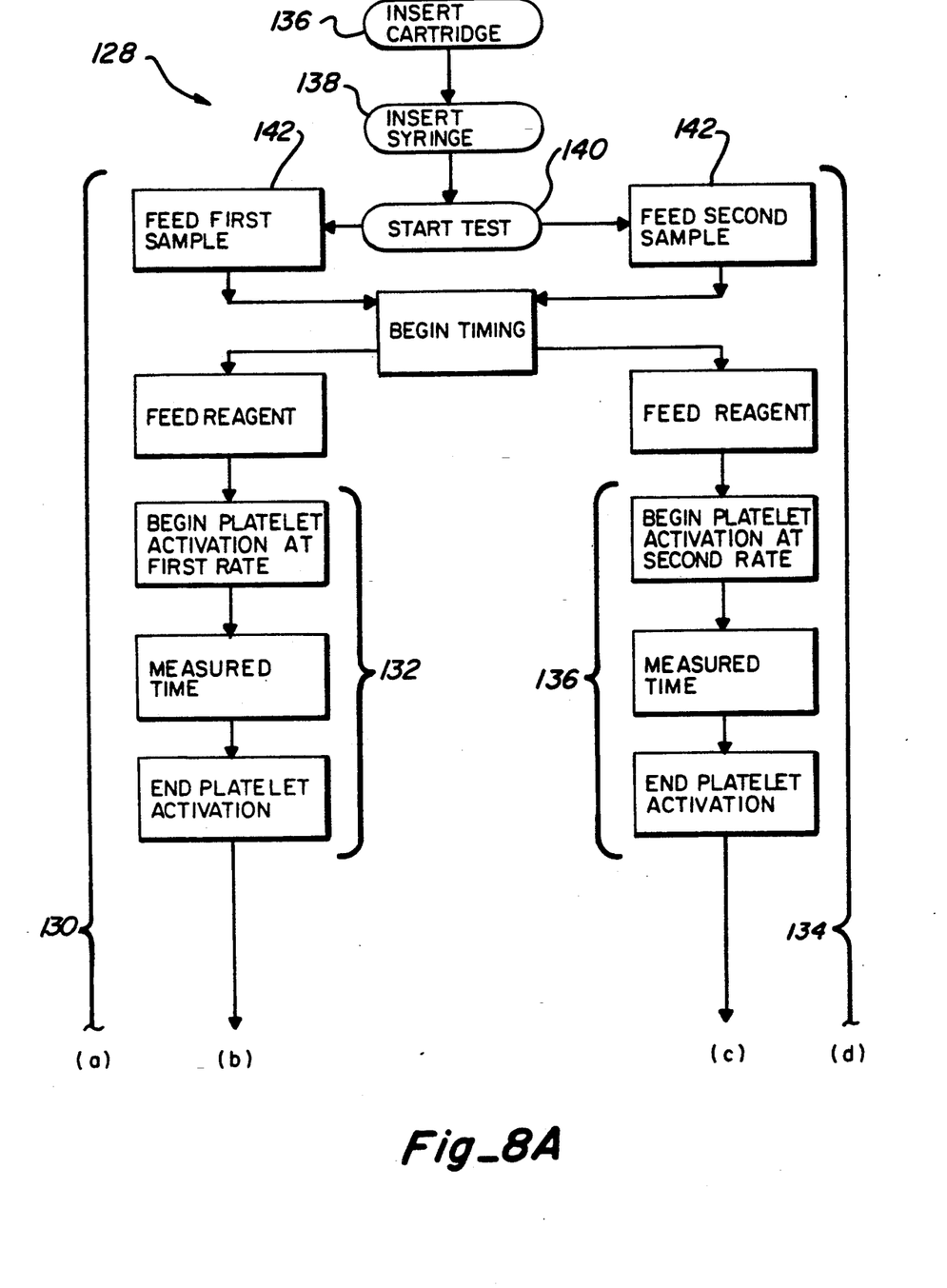
FIGS. 8A and 8B form a single flow chart of a preferred form of a clinical test for determining platelet functionality in accordance with the present invention.
Figure 8B:
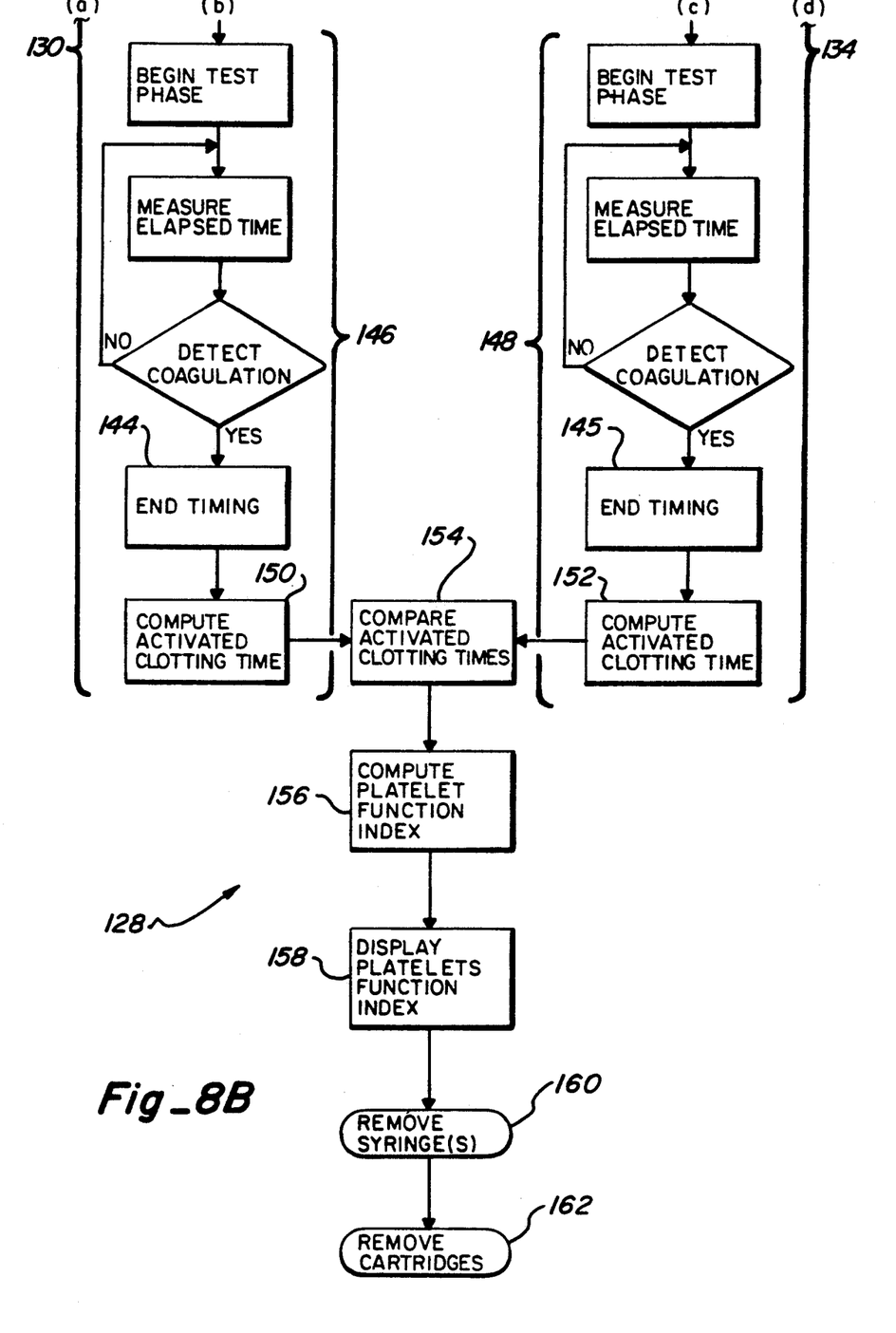

A clinical test 128 for determining the existence of functioning platelets, or the degree of platelet functionality, is performed with a plunger technique apparatus 32 and cartridge 34, is shown in FIGS. 8A and 8B and is explained in conjunction with FIGS. 3 and 4. The steps of the platelet functionality test 128 illustrated in FIGS. 8A and 8B will be referred to below by reference numbers enclosed in parentheses. The platelet functionality test 128 comprise, two ACT tests 130 and 134. In the preferred form the tests are run simultaneously. In another form the ACT tests 130 and 134 are run sequentially. The steps of the ACT tests 130 and 134 are preferably the same as the steps shown in FIG. 7, although as between the two ACT tests 130 and 134 the degree of agitation in the two platelet activation phases is different. A first ACT test (130) comprises a platelet activation phase (132) with a predetermined low intensity of agitation selected to achieve a relatively higher rate of contribution from platelet activation to the ACT. A second ACT test (134) comprises a platelet activation phase (136) with a predetermined higher intensity of agitation selected to achieve a relatively lower rate of contribution from platelet activation to the ACT.

To begin the platelet functionality index test 128 the operator inserts a cartridge 34 having at least two test cells into an ACT apparatus 32 (136). In this case the apparatus 32 has two independently operable plunger lifting subassemblies 69. A syringe 72 is inserted into the sample dispensing subassembly 74 (138) of the apparatus 32. The operator enters necessary program data into the apparatus 32 using the control switches 94 and starts the test (140) using the control switches, beginning both ACT tests simultaneously. The sample dispensing subassembly 74 of the apparatus automatically feeds substantially equal quantities of the blood sample into the reaction chamber 64 of each test cell 36 (142). The first ACT test (130) proceeds through the end of timing (144) in a manner identical to the ACT test 88 described above for FIG. 7. The second ACT test (134) proceeds through the end of timing (145) identically to the first ACT test (130) except that the rate of lifting and lowering the plunger assembly 42 during the platelet activation phase (136) of the second ACT test is more rapid than for the platelet activation phase (132) of the first test (130). In the preferred of the rate of lifting and lowering the plunger assembly 42 during the platelet activation phase (136) for the second ACT test is the same rate used to achieve high test sensitivity in the clotting test phases (146,, 148, respectively) of both the first and second ACT tests. Thus the second ACT test (134) achieves a lower rate of contribution from platelet activation to the ACT from its platelet activation phase (136), in blood samples with functional platelets.

Following the end of timing for both tests (130, 134) both ACTs are computed (150, 152), The apparatus 32 automatically compares the two ACTs (154) and computes (156) and displays (158) a platelet functionality index on the display 122 of the apparatus 32. The operator then removes the syringe 72 (160) and cartridge 34 (162) and readies the apparatus for the next test.

The preferred form of the platelet functionality index is the arithmetic difference calculated by subtracting the ACT of the first test from the ACT of the second test. Other types of platelet functionality in the form of a ratio or some other index may be calculated by performing other mathematical operations on the ACTs of the first and second tests.

An alternative form (not shown) of the platelet functionality test-comprises performing the platelet functionality test "sing two separate ACT apparatus 32 to perform the two ACT tests simultaneously. In utilizing this alternative embodiment the operator inserts cartridges 34 into the receptacles of each of the two apparatus. A syringe 72 is inserted into the sample dispensing subassembly 74 of each apparatus 32. The operator starts the platelet functionality test by starting the two ACT tests at or near the same point in time. The ACTs are displayed on the displays 122 of the apparatus 32 and the operator compares the ACTs and manually computes the platelet functionality index or otherwise judges platelet functionality.

Another alternative form (also not shown) of the platelet functionality test comprises using a single ACT test apparatus with platelet activation phase to perform the two ACT tests sequentially. The operator computes the platelet functionality index manually from the separate ACT results of the two sequential tests.

The platelet functionality test adds a new and useful element of information to that previously available to an attending physician. If functioning platelets are present in the sample being tested, the ACT for the first test (130) will be shorter than the ACT for the second test (134). The difference 28 (FIG. 2) between two ACTs is useful as an index of the platelet functionality of the sample. If the ACTs are substantially identical 30 (FIG. 2) for the first and second simultaneous tests, a lack of any substantial quantity of functional platelets in the sample is indicated.

It will be appreciated that clinical trials may establish a quantitative correlation between a platelet functionality index and any medical treatment to be administered. For example, during heart bypass surgery the platelets of blood circulated in an extracorporeal circuit are activated by the extracorporeal circuit. Once platelets are activated they lose their ability to function further. A deficiency of functional platelets in the blood may be indicative of an increased probability of a post-operative bleeding problem. Such a deficiency, and the resulting post-operative bleeding risk, could be remedied by a transfusion of platelet concentrate. The platelet functionality test can identify a deficiency of platelets or functional platelets and aid the attending physician in ascertaining when to administer a platelet concentrate transfusion. Such a test is further useful in ascertaining the efficacy of a platelet transfusion. Platelet concentrates often loose the ability to serve as a source of functional platelets during collection, storage and transfusion. By performing the platelet functionality test following a platelet transfusion it is possible to determine if additional platelet concentrate transfusions are indicated.

The preferred forms of the present invention have been described in relationship to the plunger technique is for determining ACT and in reference to a present understanding of the reasons for the utility of the present invention. It is not certain that the reasons for the functionality associated with the invention are fully understood at the present time.

A presently preferred embodiment of the present invention has been described with a degree of particularity. It should be understood that this description has been made by way of preferred example, and that the invention is defined by the scope of the following claims.

The invention claimed is:

1. A method for performing an activated clotting time test on a sample of blood containing platelets, comprising the steps of:
   combining at a single predetermined point in time an activating reagent and the sample of blood to be tested to form a test mixture at the start of the activated clotting time test;
   controllably activating the platelets of the sample during a first phase of the test by manipulating the test mixture to a predetermined degree immediately following the combining of the reagent and the sample to achieve a predetermined rate of contribution from platelet activation to the activated clotting time test;
   continuing the activated clotting time test during a second phase of the test by manipulating the test mixture to a predetermined degree difference from the predetermined degree in the first phase immediately after achieving the predetermined rate of contribution;
   terminating the activated clotting time test upon detecting a predetermined change in a property of the test mixture during the second phase which occurs as a result of the predetermined rate of contribution from platelet activation achieved during the first phase; and
   calculating the activated clotting time in specific relation to and by accounting for the predetermined rate of contribution from the platelet activation during the test.

2. A method as defined in claim 1 wherein the step of controllably activating the platelets further comprises:
   agitating the test mixture at a predetermined intensity immediately following the step of combining the reagent and the sample to achieve the predetermined rate of contribution.

3. A method as defined in claim 2 further comprising:
   selecting the predetermined intensity for agitating the test mixture to achieve an expected substantially maximum predetermined rate of contribution from platelet activation to the activated clotting time test.

4. A method as defined in claim 2 further comprising:
   selecting the predetermined intensity for agitating the test mixture to achieve a predetermined rate of contribution which is less than an expected substantially maximum predetermined rate of contribution.

5. A method as defined in claim 2 further comprising:
   controllably activating the platelets over a predetermined period of time to achieve the predetermined rate of contribution.

6. A method as described in claim 5 further comprising:
   selecting the predetermined period of time as a fixed time.

7. A method as defined in claim 1 further comprising:
   performing the activated clotting time test using a plunger sensor technique.

8. A method for performing an activated clotting time test on a sample of blood containing platelets, comprising the steps of:
   combining at a single predetermined point in time an activating reagent and the sample of blood to be tested to form a test mixture at the start of the activated clotting time test;
   controllably activating the platelets of the test mixture immediately following the combining of the reagent and the sample at a first predetermined rate to achieve a predetermined rate of contribution from platelet activation to the activated clotting time test; and
   continuing the activated clotting time test on the test mixture immediately after achieving the predetermined rate of contribution at a second predetermined rate, the second predetermined rate exceeding the first predetermined rate.

9. A method for performing an activated clotting time test on a sample of blood containing platelets using a plunger sensor apparatus, said apparatus comprising at least one test cell and a plunger assembly within said test cell, said method comprising the steps of:
   dispensing a sample of blood into the test cell;
   feeding an activating reagent into the sample of blood to form a test mixture;
   reciprocating the plunger assembly in the test mixture at a first predetermined rate for a predetermined period of time by alternately lifting the plunger assembly and allowing the plunger assembly to descent through the test mixture, the first predetermined rate of reciprocating the plunger assembly during the predetermined time period achieving a predetermined rate of contribution from platelet activation to the activated clotting time;
   immediately after expiration of the predetermined period of time, reciprocating the plunger assembly in the test mixture at a second predetermined rate by alternately lifting the plunger assembly and allowing the plunger assembly to descent through the test mixture, the second predetermined rate being different than the first predetermined rate;
   detecting a point in time at which a predetermined property of the test mixture changes by a predetermined expected amount by sensing the descent of the plunger assembly, the predetermined property affecting the activated clotting time test;
   measuring an elapsed time from the beginning of the step of feeding the reagent to the point in time at which the property of the test mixture changes by the predetermined expected amount; and
   calculating the activated clotting time of the sample of blood based on the elapsed time in specific relation to and by accounting for the predetermined rate of contribution from the platelet activation to the activated clotting time during the test.

10. A method as defined in claim 9 further comprising:
    selecting the first predetermined rate of reciprocating the plunger assembly in the test mixture to achieve an expected substantially maximum predetermined rate of contribution from platelet activation during the predetermined time period to the activated clotting time from a sample of normal blood.

11. A method as defined in claim 9 further comprising:

selecting the first predetermined rate of reciprocating the plunger assembly in the test mixture to achieve a predetermined range of contribution from platelet activation during the predetermined time period which is less than an expected predetermined maximum rate of contribution from a sample of normal blood.

12. A method as defined in claim 9 further comprising:

selecting the predetermined period of time to be within the range of approximately thirty to forty seconds.

13. A method for performing an activated clotting time test on a sample of blood containing platelets using a plunger sensor apparatus, said apparatus comprising at least one test cell and a plunger assembly within said test cell, said method comprising the steps of:

dispensing a sample of blood into the test cell;

feeding an activating reagent into the sample of blood to form a test mixture;

reciprocating the plunger assembly in the test mixture at a first predetermined rate for a predetermined period of time by alternately lifting the plunger assembly and allowing the plunger assembly to descend through the test mixture, the first predetermined rate of reciprocating the plunger assembly during the predetermined time period achieving a predetermined rate of contribution from platelet activation to the activated clotting time;

immediately after expiration of the predetermined period of time, reciprocating the plunger assembly in the test mixture at a second predetermined rate by alternately lifting the plunger assembly and allowing the plunger assembly to descend through the test mixture, the second predetermined rate being different than the first predetermined rate;

detecting a point in time at which a predetermined property of the test mixture changes by a predetermined expected amount by sensing the descent of the plunger assembly, the predetermined property affecting the activated clotting time test;

measuring an elapsed time from the beginning of the step of feeding the reagent to the point in time at which the property of the test mixture changes by the predetermined expected amount;

calculating the activated clotting time of the sample of blood based on the elapsed time; and selecting the second predetermined rate of reciprocating the plunger assembly to be greater than the first predetermined rate.

14. A method as defined in claim 9 wherein the step of calculating the activated clotting time further comprises:

establishing the activated clotting time as equal to the elapsed time.

15. A method of evaluating platelet functionality on blood containing platelets, comprising the steps of:

performing a first activated clotting time test on a first sample of the blood by steps including:

controllably activating the platelets of the first sample to normally achieve a first predetermined rate of contribution from platelet activation to an activated clotting time test; and measuring an activated clotting time on the first sample;

performing a second activated clotting time test on a second sample of the blood by steps including:

controllably activating the platelets of the second sample to normally achieve a second predetermined rate of contribution from platelet activation to an activated clotting time test, the second predetermined rate of contribution being less than the first predetermined rate of contribution; and measuring an activated clotting time on the second sample; and comparing the activated clotting times measured on the first and second samples to evaluate the platelet functionality of the blood.

16. A method as defined in claim 15 where in the comparing step further comprises:

subtracting the activated clotting times of the first and second samples to establish a platelet functionality index.

17. A method as defined in claim 15 further comprising:

performing the first activated clotting time test and the second activated clotting time test simultaneously.

18. A method as defined in claim 15 further comprising:

measuring the activated clotting times of the first and second samples immediately after controllably activating the platelets of each of the first and second samples to achieve the first and second ranges of contribution, respectively.

19. A method as defined in claim 18 further comprising:

combining an activating reagent with each of the first and second samples immediately prior to controllably activating the platelets in each of the first and second samples.

20. A method as defined in claim 15 further comprising:

combining an activating reagent with each of the first and second samples immediately prior to controllably activating the platelets in each of the first and second samples.

21. A method as defined in claim 15 further comprising:

performing the first and second activated clotting time tests on the first and second samples simultaneously.

22. A method as defined in claim 15 wherein the step of controllably activating the platelets of the first sample further comprises:

combining the first sample with an activating reagent to form a first test mixture; and agitating the first test mixture at a first predetermined intensity immediately following the step of combining the activating reagent and the first sample; and the step of activating the platelets of the second sample further comprises:

combining the second sample with an activating reagent to form a second test mixture; and activating the second test mixture at a second predetermined intensity immediately following the step of combining the activating reagent and the second sample; and the first and second predetermined intensities are different.

23. A method of claim 22 further comprising:
selecting the predetermined intensity of activating the first test mixture during the step of activating the platelets of the first test mixture to achieve an expected substantially maximum predetermined rate of contribution from platelet activation to the activated clotting time from a sample of normal blood; and
selecting the predetermined intensity of activating the second test mixture during the step of activating the platelets of the second test mixture to achieve a predetermined rate which is less than expected maximum rate of contribution from platelet activation to the activated clotting time from a sample of normal blood.

24. A method as defined in claim 22 further comprising:
selecting the predetermined intensity of activating the first test mixture to achieve a predetermined rate greater than an expected minimum range of contribution from platelet activation to the activated clotting time from a sample of normal blood; and
selecting the predetermined intensity of activating the second test mixture to achieve an expected substantially minimum range of contribution from platelet activation to the activated clotting time from a sample of normal blood.

25. A method as defined in claim 22 wherein:
the step of controllably activating the platelets of the first and second test mixtures proceeds over a first and a second predetermined period of time, respectively.

26. A method as defined in claim 25 wherein the first and second predetermined time periods are approximately equal.

27. A method as defined in claim 26 wherein the first and second predetermined periods of time are within the range of approximately thirty to forty seconds.

28. A method as defined in claim 15 further comprising:
performing the first and second activating clotting time tests by using a plunger sensor technique for each test.

29. A method as defined in claim 15 performed using a plunger sensor apparatus, said apparatus comprising a first test cell having a first plunger assembly therein and a second test cell having a second plunger assembly therein, said method comprising the steps of:
dispensing the first and second samples into the first and second test cells, respectively;
performing the first activated clotting time test on the first sample by steps further comprising:
combining an activating reagent with the first sample to form a first test mixture;
reciprocating the first predetermined plunger in the first test mixture at a first predetermined rate for a first predetermined period of time by alternately lifting the plunger assembly and allowing the plunger assembly to descent through the first test mixture;
immediately after the first predetermined time period, reciprocating the first predetermined plunger in the first test mixture at a second predetermined rate by alternately lifting the predetermined plunger and allowing the predetermined plunger to descent through the first test mixture;
detecting a point in time at which a predetermined property of the first test mixture changes by a predetermined amount to slow the descent of the first plunger assembly by a predetermined amount, the predetermined property related to platelet activation of the blood in the first test mixture; and
measuring a first elapsed time from the beginning of the step of combining the activating reagent to the point in time at which the descent of the first plunger assembly is slowed by the predetermined amount;
performing a second activated clotting the time test on the second sample by steps further comprising:
combining an activating reagent with the second sample to form a second test mixture;
reciprocating the second plunger assembly in the second test mixture at a third predetermined rate for a second predetermined period of time by alternately lifting the plunger assembly and allowing the plunger assembly to descend through the second test mixture;
immediately after the second predetermined time period, reciprocating the second plunger assembly in the second test mixture at a fourth predetermined rate by alternately lifting the plunger assembly and allowing the plunger assembly to descend through the second test mixture;
detecting a point in time at which a predetermined property of the first test mixture changes by a predetermined amount to slow the descent of the second plunger assembly by a predetermined amount, the predetermined property related to platelet activation of the blood in the second test mixture; and
measuring a second elapsed time from the beginning of the step of combining the activating reagent to the point in time at which the descent of the second plunger assembly is slowed by the predetermined amount;
comparing the first and the second elapsed times; and
evaluating the platelet functionality based on the comparison of the first and second elapsed times.

30. A method as defined in claim 29 further comprising:
selecting the first predetermined rate of reciprocating the first plunger assembly in the first test mixture to normally achieve a predetermined expected substantially maximum rate of contribution from platelet activation to the activated clotting time.

31. A method as defined in claim 29 further comprising:
selecting the first predetermined rate of reciprocating the first plunger assembly in the first test mixture to achieve a predetermined rate which is substantially less than the expected maximum rate of contribution of platelet activation tot he activated clotting time.

32. A method as defined in claim 29 further comprising:
extending each one of the first and second predetermined periods of time to be within the range of thirty to approximately forty seconds.

33. A method as defined in claim 29 further comprising:
selecting the third predetermined rate of reciprocating the second plunger assembly in the second test mixture to achieve a predetermined expected substantially minimum rate of contribution of platelet activation to the activated clotting time.

34. A method as defined in claim 29 further comprising:
selecting the second, third and fourth predetermined rates of reciprocating the corresponding plunger assembly to be substantially equal.

35. A method as defined in claim 29 further comprising:
selecting the second, third and fourth predetermined rates of reciprocating the corresponding plunger assembly to be greater than the first predetermined rate of reciprocating the first plunger assembly.

36. A method as defined in claim 29 further comprising:
subtracting the first elapsed time from the second elapsed time.

37. A method as defined in claim 29 further comprising:
performing the activated clotting time of the first sample simultaneously with the step of performing the activated clotting time of the second sample.

38. A method for diagnosing platelet activation functionality in a patient comprising the steps of:
taking a sample of the patient's blood; and
performing a platelet functionality test on the sample of blood, said platelet functionality test further comprising:
dividing the sample of blood into first and second partial samples;
performing a first activated clotting time test on the first partial sample after manipulating the first partial sample to normally activate platelets to achieve a first predetermined rate of contribution to the activated clotting time;
performing a second activated clotting time test on the second partial sample after manipulating the second partial sample to normally activate platelets to achieve a second predetermined rate of contribution to the activated clotting time, the first and second predetermined rates being different; and
determining platelet functionality based on the difference in activated clotting times of the first and second partial samples.

39. A method as defined in claim 38 further comprising:
administering a transfusion of one of platelet concentrate, blood containing platelets or components of blood containing platelets based on the platelet functionality test.

40. A method as defined in claim 39 further comprising diagnosing the effectiveness of the transfusion by steps comprising:
taking an additional sample of the patient's blood after the step of administering the transfusion; and
repeating the aforementioned steps using the additional sample to determine platelet functionality as a result of the transfusion.

41. An apparatus for performing a platelet functionality test on blood containing platelets using a plunger sensor technique, said apparatus comprising a cartridge having first and second test cells and first and second plunger assemblies in the first and second test cells, respectively, each test cell further containing an activating reagent, said apparatus further comprising:
dispensing means for dispensing first and second samples of the blood into the first and second test cells;
first reagent drive means for combining the activating reagent with the first sample to form a first test mixture in the first test cell;
first plunger lifting means for reciprocating the first plunger assembly in the first test mixture at a first predetermined rate for a first predetermined period of time by alternately lifting the plunger assembly and allowing the plunger assembly to descend through the first test mixture, and for reciprocating the first plunger assembly in the first test mixture at a second predetermined rate after the expiration of the first predetermined time period by alternately lifting the plunger assembly and allowing the plunger assembly to descend through the first test mixture, the first predetermined rate of reciprocating the plunger assembly during the first predetermined time period achieving a predetermined rate of contribution to clotting of the sample from platelet activation;
detection means for detecting a point in time at which a property of the first sample changes by a predetermined amount to slow the descent of the first plunger assembly by a predetermined amount, the predetermined property relating to the functionality of the platelets in the first sample;
means for measuring a first elapsed time from a point in time at which the activating reagent is combined with the first sample to the point in time at which the descent of the first plunger assembly is slowed by the predetermined amount;
second reagent drive means for combining the activating reagent with the second sample to form a second test mixture in the second test cell;
second plunger lifting means for reciprocating the second plunger assembly in the second test mixture at a third predetermined rate for a second predetermined period of time by alternately lifting the plunger assembly and allowing the plunger assembly to descend through the second test mixture, and for reciprocating the second plunger assembly in the second test mixture at a fourth predetermined rate after the expiration of the second predetermined time period by alternately lifting the plunger assembly and allowing the plunger assembly to descend through the second test mixture, the third predetermined rate of reciprocating the plunger assembly during the second predetermined time period achieving a predetermined rate of contribution to clotting of the second sample from platelet activation;
detection means for detecting the point in time at which a property of the second sample changes by a predetermined amount to slow the descent of the second plunger assembly by a predetermined amount, the predetermined property relating to the functionality of the platelets in the second sample;
means for measuring a second elapsed time from a point in time at which the activating reagent is combined with the second sample to the point in time at which the descent of the second plunger assembly is slowed by the predetermined amount;
the first and second plunger reciprocating means operating simultaneously, the first rate and the third rate of reciprocating the first and second plunger assemblies being different; and
display means for displaying information related to the first and second elapsed times by which to evaluate the platelet functionality of the blood.

42. An apparatus as defined in claim 41 wherein:
the first predetermined rate of reciprocating the first plunger assembly in the first test mixture achieves a predetermined expected substantially maximum rate of contribution from platelet activation to activated clotting time from the first sample of normal blood.

43. An apparatus as defined in claim 41 wherein:

the first and second reagent drive means operate to respectively combine the activating reagent with the first and second samples simultaneously; and the first and second lifting plunger means commence reciprocating the first and second plunger assemblies at the first and third rates, respectively, immediately after the combination of the activating agent with the first and second samples.

44. An apparatus as defined in claim 41 wherein:

the first and second reagent drive means comprise portions of a single reagent drive means.

* * * * *